(12) United States Patent
Berry et al.

(10) Patent No.: US 7,297,787 B2
(45) Date of Patent: Nov. 20, 2007

(54) PROCESS FOR PREPARING N6 SUBSTITUTED AMINOPURINE RIBOFURANOSE NUCLEOSIDES

(75) Inventors: Malcolm Berry, Stevenage (GB); John C. Roberts, Durham, NC (US); Shiping Xie, Durham, NC (US)

(73) Assignee: Glaxo Group Limited, Greenford, Middlesex (GB)

(*) Notice: Subject to any disclaimer, the term of this patent is extended or adjusted under 35 U.S.C. 154(b) by 714 days.

(21) Appl. No.: 10/471,682

(22) PCT Filed: Mar. 19, 2002

(86) PCT No.: PCT/GB02/01344

§ 371 (c)(1),
(2), (4) Date: Sep. 12, 2003

(87) PCT Pub. No.: WO02/074781

PCT Pub. Date: Sep. 26, 2002

(65) Prior Publication Data

US 2005/0176949 A1    Aug. 11, 2005

(30) Foreign Application Priority Data

Mar. 20, 2001 (GB) ................. 0106867.5

(51) Int. Cl.
*C07H 19/167* (2006.01)
(52) U.S. Cl. .................. 536/27.11; 536/27.3; 536/124
(58) Field of Classification Search ............. 536/27.11, 536/27.3, 124
See application file for complete search history.

(56) References Cited

U.S. PATENT DOCUMENTS 6,492,348 B1 * 12/2002 Bays et al. .................. 514/46
6,677,316 B2 * 1/2004 Bays et al. .................. 514/46

FOREIGN PATENT DOCUMENTS

| EP | 0 322 242 | 6/1989 |
|----|-----------|--------|
| WO | 97/43300  | 11/1997 |
| WO | 98/01426  | 1/1998 |
| WO | 98/01459  | 1/1998 |
| WO | 98/16539  | 4/1998 |
| WO | 99/24449  | 5/1999 |
| WO | 99/24450  | 5/1999 |
| WO | 99/24451  | 5/1999 |
| WO | 99/67262  | 12/1999 |
| WO | 00/75158  | 12/2000 |

OTHER PUBLICATIONS

Fleysher, M. H. et al., "Synthesis and Biological Activity of Some New N6-Substituted Purine Nucleosides," *J. Med. Chem.*, vol. 12, 1969, pp. 1056-1061.

Fleysher, M. H., "N6-Substituted adenosines: synthesis, biological activity, and some structure-activity relationships," *Journal of Medicinal Chemistry*, vol. 15, No. 2, 1972, pp. 187-191.

Fleysher, M.H. et al., "Some Short-Chain N6-Substituted Adenosine Analogues with Antitumor Properties," *J. Med. Chem.*, vol. 23, 1980, pp. 1448-1452.

Kwatra, M.M., et al., "N6-Phenlyadenosines: Profound Effect of Phenyl Substituents on Affinity for A2 Adenosine Receptors," *J. Med. Chem.*, vol. 30, 1987, pp. 954-956.

Gallo-Rodriguez, C., et al., "Structure Activity Relationships of N6-Benzyladenosine-5'-uronamides as A3 Selective Adenosine Agonists," *Journal of Medicinal Chemistry*, vol. 37, No. 5, Mar. 4, 1994, pp. 636-646.

* cited by examiner

Primary Examiner—S. Anna Jiang
Assistant Examiner—L. E. Crane
(74) Attorney, Agent, or Firm—Bonnie L. Deppenbrock

(57) ABSTRACT

An improved process for preparing N6-substituted aminopurine ribofuranose nucleosides. Compounds of this type are known to be usefull in the prepartation of compounds having activity at adenosine receptors, e.g. Adenosine A1 receptor. The process comprises the step of reacting a 6-halopurine ribofuranose nucleoside with an amine in the presence of $CaCO_3$, wherein acid is added to the reaction mixture.

5 Claims, No Drawings

PROCESS FOR PREPARING N6 SUBSTITUTED AMINOPURINE RIBOFURANOSE NUCLEOSIDES

CROSS-REFERENCE TO RELATED APPLICATIONS

This application is filed pursuant to 35 USC 371 as a United States National Phase Application of International Patent Application Serial No. PCT/GB02/01344 filed on Mar. 19, 2002, which claims priority from 0106867.5 filed on Mar. 20, 2001 in the United Kingdom.

FIELD OF THE INVENTION

The present invention relates to an improved process for the preparation of $N^6$-substituted aminopurine ribofuranose nucleosides. More particularly, the invention is concerned with an improved process for preparing $N^6$-substituted aminopurine ribofuranose nucleosides by amination of the corresponding 6-halopurine ribofuranose nucleoside in the presence of $CaCO_3$. Compounds of this type are known to be useful in the preparation of compounds having activity at adenosine receptors, e.g. the Adenosine A1 receptor.

BACKGROUND OF THE INVENTION

Adenosine A1 agonists and processes for their preparation are described in: EP0322242, WO97/43300, WO99/24449, WO99/24450, WO99/24452, WO99/67262, WO98/16539 (Novo Nordisk A/S); WO98/04126 (Rhone-Poulenc Rorer Pharmaceuticals Inc.); and WO98/01459 (Novo Nordisk A/S). For example, in WO99/67262 (Glaxo Group Limited), adenosine derivatives are prepared by reaction of a halopurine ribofuranose nucleoside with an amine either in the absence or presence of a solvent such as an alcohol, an ether, a substituted amide, a halogenated hydrocarbon, an aromatic hydrocarbon, dimethyl sulfoxide (DMSO) or acetonitrile, preferably at an elevated temperature, in the presence of a suitable acid scavenger, for example, inorganic bases such as sodium, cesium or potassium carbonate, or organic bases such as triethylamine, diisopropylethylamine or pyridine, optionally in the presence of a palladium catalyst and phosphine ligand.

An alternative process for the preparation of arylamines is described in U.S. Pat. No. 5,576,460 (Buchwald). This process involves reacting an amine with an aryl halide compound in the presence of a nickel or palladium catalyst. The present inventors found, however, that when reacting 6-halopurine ribofuranose nucleosides with certain amines (e.g. 4-chloro-2-fluoroaniline), the process had low reproducibility and tended to give incomplete reaction and very low yield. The incomplete reaction, in addition to the necessity of removing the palladium heavy metal makes the process impractical for preparing certain 6-substituted aminopurine ribofuranose nucleosides.

$CaCO_3$ processes for preparing adenosine derivatives are described in Kwatra et al., (1987) *J. Med. Chem.* 30:954, Fleysher et al., (1969) *J. Med. Chem.* 12:1056 and Yadava et al. (1988) *Himalayan Chem. Pharm Bull.* 5:31. For example, Fleysher et al. describes the synthesis of $N^6$-phenyladenosine from 6-chloropurine riboside in absolute ethanol in the presence of $CaCO_3$. However, the present inventors found that when anilines of poor nucleophilicity like 4-cholor-2-fluoroaniline were reacted with 6-chloropurine riboside under these conditions, the reaction was slow and a significant amount of $N^6$-arylladenine by-product was derived from cleavage of the glycosyl linkage. The reaction was also found to be sensitive to the choice of solvents, for example, it had no meaningful conversion in 2-methoxyethanol and provided only 25% yield of product in isopropanol.

The problem to be solved by the present invention was therefore to provide an improved process for the preparation of $N^6$-substituted aminopurine ribofuranose nucleosides.

SUMMARY OF THE INVENTION

The present inventors have surprisingly found that when a $CaCO_3$ process is used for preparing $N^6$-substituted aminopurine ribofuranose nucleosides, the addition of acid at the start of the reaction accelerates the reaction, improves the yield, and/or reduces the quantity of acid hydrolysis by-products generated. It is surprising that the addition of acid improves the efficiency of the reaction instead of neutralising the base ($CaCO_3$) and preventing the reaction. Previously, $CaCO_3$ had been used as an acid scavenger (base) to promote reactions in which an acid was generated.

Accordingly, the present invention provides a process for preparing $N^6$-substituted aminopurine ribofuranose nucleosides comprising the step of reacting a 6-halopurine ribofuranose nucleoside (e.g. a 6-chloropurine ribofuranose nucleoside) with an amine (e.g. an aliphatic amine, alicyclic amine or aromatic amine) in the presence of $CaCO_3$, characterised in that acid is added to the reaction mixture at the start of the reaction.

A further aspect of the invention is the use of the process of the invention in the preparation of compounds which have activity at adenosine receptors, e.g. the Adenosine A1 receptor.

DETAILED DESCRIPTION OF THE INVENTION

A preferred aspect of the invention is the use of the process of the invention in the preparation of $N^6$-aminopurine ribofuranose nucleosides as described in EP0322242, WO97/43300, WO99/24449, WO99/24450, WO99/24452, WO99/67262, WO98/16539 (Novo Nordisk A/S); WO98/04126 (Rhone-Poulenc Rorer Pharmaceuticals Inc.); and WO98/01459 (Novo Nordisk A/S) which are all incorporated herein by reference in their entirety.

Another preferred aspect of the invention is a process for preparing a $N^6$-substituted aminopurine ribofuranose nucleoside of formula (I):

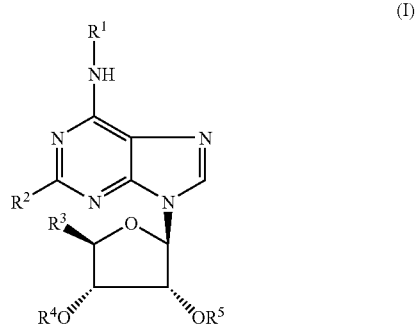

comprising the step of reacting a 6-halopurine ribofuranose nucleoside of formula (II) with an amine of formula (III) in the presence of $CaCO_3$, characterised in that acid is added to the reaction mixture at the start of the reaction;

wherein the 6-halopurine ribofuranose nucleoside of formula (II) and the amine of formula (III) are:

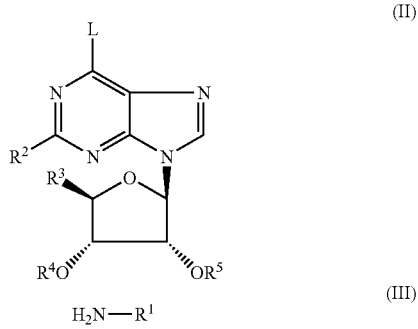

(II)

(III)

wherein L represents halogen;

$R^2$ represents $C_{1-3}$alkyl, $C_{1-3}$alkenyl, $C_{1-3}$alkoxy, halogen or hydrogen;

$R^3$ represents (i) hydrogen, (ii) $C_{1-6}$alkyl optionally substituted by one or more halogens, (iii) $C_{1-6}$ alkylOCH$_2$— where the alkyl chain is optionally substituted by one or more halogens, (iv) an acetylene group, or (v) a 5-membered heterocyclic group optionally substituted by: $C_{1-6}$alkoxy-, —$C_{1-6}$alkylO(CH$_2$)$_n$— where n is 0-6, $C_{3-7}$cycloalkyl, $C_{1-6}$hydroxyalkyl, halogen or a —$C_{1-6}$ alkyl, —$C_{1-6}$alkenyl or —$C_{1-6}$alkynyl group optionally substituted by one or more halogens;

$R^4$ and $R^5$ independently represent hydrogen, acyl, —$C_{1-6}$ alkyl or a suitable protecting group (e.g. acetyl or a protecting group wherein $R^4$ and $R^5$ together form an alkylidene group);

$R^1$ represents hydrogen or a group selected from:
(i) -(alk)$_n$-(C$_{3-9}$)cycloalkyl or -(alk)$_n$-(C$_{3-9}$)cycloalkenyl, said cycloalkyl or cycloalkenyl group being optionally substituted by one or more substituents selected from OH, halogen, $C_{1-6}$alkyl, —$C_{1-6}$alkoxy, $C_{2-6}$alkenyloxy-, $C_{2-6}$ alkynyloxy-, and phenyl, wherein (alk) represents $C_{1-3}$alkyl and n represents 0 or 1, and said (alk) group may be optionally substituted by a $C_{3-6}$cycloalkyl group;
(ii) a phenyl group optionally substituted by one or more substituents selected from: halogen, OH, CF$_3$, cyano, —$C_{1-6}$alkyl, —$C_{2-6}$alkenyl, —$C_{2-6}$alkynyl, $C_{1-6}$alkoxy-, —$C_{1-6}$alkylOH, —CO$_2$H and —CO$_2$C$_{1-6}$ alkyl;
(iii) a $C_{4-7}$aliphatic heterocyclic group containing at least one heteroatom selected from O, N and S, and optionally substituted by one or more substituents selected from: OH, —$C_{1-6}$alkyl, —$C_{1-6}$alkoxy, —CO$_2$(C$_{1-4}$)alkyl, —CO (C$_{1-4}$)alkyl, —CO$_2$aryl, and —CO$_2$(alk)$_n$(C$_{3-6}$)cycloalkyl, wherein (alk) is $C_{1-3}$alkyl and n represents 0 or 1;
(iv) a straight or branched $C_{1-12}$alkyl group optionally substituted by one or more groups selected from phenyl, halogen, hydroxy, and $C_{3-7}$ cycloalkyl, wherein one or more carbon atoms of the $C_{1-12}$alkyl group may be optionally replaced by a group independently selected from S(=O)$_n$ (where n is 0, 1 or 2) and N; and
(v) a fused bicyclic ring

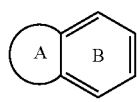

wherein A represents $C_{4-6}$ cycloalkyl or phenyl and B represents phenyl optionally substituted by $C_{1-3}$alkyl, and the bicyclic ring is attached to the purine-6-amino moiety via a ring atom of ring A.

In an alternative aspect $R^1$ represents:
(i) -(alk)$_n$-(C$_{3-9}$)cycloalkyl, including bridged cycloalkyl, optionally substituted by one or more substituents selected from: OH, halogen, —$C_{1-3}$alkoxy, or phenyl wherein (alk) represents $C_{1-3}$alkyl or $C_{1-3}$alkylene and n represents 0 or 1;
(ii) a $C_{4-7}$aliphatic heterocyclic group containing at least one heteroatom selected from O, N or S, and optionally substituted by one or more subsituents selected from: OH, —$C_{1-6}$alkyl, —$C_{1-6}$alkoxy —CO$_2$(C$_{1-4}$)alkyl, and —CO (C$_{1-3}$alkyl);
(iii) a straight or branched $C_{1-12}$ alkyl, optionally including one or more O, S(=O)$_n$ (where n is 0, 1 or 2) and N groups substituted within the alkyl chain, said alkyl optionally substituted by one or more of the following groups: phenyl, halogen, hydroxy or $C_{3-7}$cycloalkyl;
(iv) a phenyl group optionally substituted by one or more substituents selected from: halogen, CF$_3$, cyano, —$C_{1-6}$ alkyl, —$C_{2-6}$ alkenyl, —$C_{1-6}$alkoxy, —$C_{1-6}$ alkylOH, —CO$_2$H and —CO$_2$C$_{1-6}$ alkyl.

As used herein, the terms "alkyl" and "alkoxy" mean both straight and branched chain saturated hydrocarbon groups. Examples of alkyl groups include methyl, ethyl, propyl and butyl groups. Examples of alkoxy groups include methoxy and ethoxy groups. Other examples include propoxy and butoxy. The term "hydroxyalkyl" means both straight and branched chain saturated hydrocarbon groups substituted by a hydroxy group. Alkyl groups may be unsubstituted, or substituted with one to four substituents, preferably one to three substituents as defined hereinabove.

One to three, preferably one or two, carbon atoms of an alkyl chain may be replaced by a group independently selected from S(=O)$_n$ (where n is 0, 1 or 2) and N. When the heteroatom N replaces a carbon atom in a $C_{1-12}$alkyl group the N atom will, where appropriate be substituted by one or two substituents selected from hydrogen and $C_{1-6}$alkyl.

As used herein, the terms "alkenyl", "alkynyl", "alkenyloxy" and "alkynyloxy" mean both straight and branched chain unsaturated hydrocarbon groups. Examples of alkenyl groups include ethylene and propylene. Examples of alkynyl groups include ethynyl and propynyl. Examples of alkynyloxy groups include propynyloxy and ethynyloxy. Examples of alkenyloxy groups include propenyloxy and ethenyloxy.

As used herein, the term "halo" or 'halogen' means fluorine, chlorine, bromine or iodine.

As used herein, the term "acyl" means a straight or branched $C_{1-6}$alkyl-C=O group.

As used herein the term "aryl" means monocyclic or bicyclic aromatic carbocyclic groups such as phenyl or naphthyl, preferably phenyl.

As used herein, the term "cycloalkyl" means an aliphatic group preferably having 3 to 9 carbon atoms in the ring system. The cycloalkyl group can be monocyclic or bicyclic. A bicyclic group may be fused or bridged. Preferably, the cycloalkyl group is monocyclic. Examples of monocyclic cycloalkyl groups include cyclopropyl, cyclobutyl, cyclopentyl, cyclohexyl and cycloheptyl. Another example of a monocyclic cycloalkyl group is cyclooctyl. Examples of bicyclic cycloalkyl groups include bicyclo[2.2.1]hept-2-yl. Cycloalkyl groups may be unsubstituted, or substituted with one to four substituents, preferably one or two substituents as defined hereinabove.

As used herein, the term "cycloalkenyl" means a partially unsaturated aliphatic group having 3 to 9 carbon atoms in the ring system. The cycloalkenyl group can be monocyclic or bicyclic. Preferably, the cycloalkyl group is monocyclic. Examples of monocyclic cycloalkenyl groups include cyclopentenyl and cyclohexenyl. Cycloalkenyl groups may be unsubstituted, or substituted with one to four substituents, preferably one or two substituents as defined hereinabove.

As used herein, the term "heterocyclic group" means rings containing one or more heteroatoms selected from: nitrogen, sulphur and oxygen. The heterocycle may be aromatic or non-aromatic, i.e., may be saturated, partially or fully unsaturated. Examples of 5-membered groups include isoxazole, oxadiazole, pyrazole, oxazole, triazole, tetrazole and thiadiazole.

When the heteroatom N replaces a carbon atom in a $C_{1-12}$alkyl group the N atom will, where appropriate be substituted by one or two substituents selected from hydrogen and $C_{1-6}$alkyl.

As used herein, the term "aliphatic heterocyclic group" as defined for $R^1$ means a cyclic group of 4 to 7 carbon atoms wherein one or more of the carbon atoms is/are replaced by heteroatoms independently selected from nitrogen, oxygen or sulfur. This group may be unsubstituted, or substituted with one to four substituents, preferably one or two substituents as defined hereinabove. Examples of aliphatic heterocyclic groups include piperidinyl, tetrahydrofuranyl and tetrahydropyranyl.

As used herein, the term "aliphatic amine" means an amine group comprising straight or branched chains of carbon atoms, saturated or unsaturated.

As used herein, the term "alicyclic amine" means an amine group comprising at least one closed ring of carbon atoms, e.g. cycloalkyl groups.

As used herein, the term "aromatic amine" means an amine group comprising at least one benzene ring.

Preferably, L represents chlorine.

Preferably, $R^2$ represents halogen or hydrogen, more preferably hydrogen.

Preferably, $R^3$ represents an acetylene group, or a 5-membered heterocyclic group optionally substituted by a $C_{1-4}$alkyl. Preferably the heterocyclic group is selected from an isoxazole, oxadiazole, pyrazole, oxazole, triazole, tetrazole or thiadiazole, more preferably an isoxazole, a 1,2,4- or 1,3,4-oxadiazole.

Preferably $R^4$ and $R^5$ represent hydrogen, or together form an alkylidene group. More preferably, $R^4$ and $R^5$ together form an alkylidene group.

Conveniently, $R^1$ may represent $(alk)_n$-$C_{3-9}$cycloalkyl wherein n is 0 or 1 and the said cycloalkyl is either unsubstituted or substituted by at least one substituent selected from halogen, particularly fluorine, and OH. Alternatively the cycloalkyl group may be either unsubstituted or substituted by at least one substituent selected from —$C_{1-6}$alkyl, $C_{1-6}$alkoxy-, phenyl and OH. Further alternative substituents include at least one substituent selected from halogen, $C_{2-6}$alkenyloxy-, and —$C_{3-6}$ cycloalkyl. More preferably, the cycloalkyl group is unsubstituted or monosubstituted with OH or $C_{1-3}$ alkyl, yet more preferably by OH. The cycloalkyl group may also be monosubstituted by $C_{2-6}$alkenyloxy- or —$C_{3-6}$cycloalkyl, or substituted by one or two halogen atoms. Preferably the cycloalkyl ring has 3 to 8 carbon atoms, more preferably 5 or 6 carbon atoms. Cycloalkyl groups include hydroxycyclopentyl or methoxycyclohexyl. Other cycloalkyl groups include propenyloxycyclohexyl, ethyloxycyclohexyl, difluorocyclohexyl, dicyclopropylmethyl, cyclooctyl and cycloheptyl. Preferably n is zero. When n is 1 and the (alk) group is substituted, substituents include cyclopropyl.

$R^1$ may represent $(alk)_n$-$(C_{3-9})$cycloalkenyl wherein n is 0 or 1 and the said cycloalkenyl is unsubstituted or substituted by at least one substituent selected from —$C_{1-6}$alkyl, $C_{1-6}$alkoxy-, phenyl and OH. Alternative substituents include at least one substituent selected from halogen, —$C_{2-6}$ alkenyloxy, and —$C_{3-6}$cycloalkyl. Preferably n is zero. More preferably, the cycloalkenyl group is unsubstituted. Preferably the cycloalkenyl ring has 5 or 6 carbon atoms, more preferably the ring is cyclohexenyl.

Alternatively, $R^1$ may represent a substituted or unsubstituted aliphatic heterocyclic group, the substitutent being selected from $C_{1-6}$alkyl, or —$CO_2(C_{1-4})$alkyl. The substituent may also be —$CO_2$phenyl or —$CO_2(alk)_n(C_{3-6})$cycloalkyl. Preferably the aliphatic heterocyclic ring is 6 membered and more preferably contains only one O, N or S heteroatom. Conveniently, the aliphatic heterocyclic group is unsubstituted or, when substituted, the substituent is —$CO_2(C_{1-4})$alkyl or —$CO_2(alk)_n(C_{3-6})$cycloalkyl or —$CO_2$phenyl, the heteroatom is N and the substituent is directly attached to said ring nitrogen atom. Preferably when the heterocycle is substituted with —$CO_2(C_{1-4})$alkyl, the heteroatom is N and the substituent is directly attached to said ring nitrogen atom. Most preferably when the heterocyclic ring is unsubstituted the heteroatom is O. Most preferably when the heterocyclic ring is substituted the heteroatom is N.

Alternatively, $R^1$ may represent a straight or branched alkyl of 1-6 carbon atoms optionally with at least one $S(=O)_n$ and where $S(=O)_n$ is present, optionally substituted with N at a position adjacent to the $S(=O)_n$ group; where there is an group is preferred; where there is an $S(=O)_n$ in the chain, preferably n is 1 or 2, more preferably n is 2. The alkyl group conveniently may be unsubstituted or substituted by at least one OH group.

Alternatively $R^1$ may represent a phenyl group which is substituted by one or two substituents selected from OH, $C_{1-6}$alkyl, particularly $C_{1-4}$alkyl and halogen. Preferably the phenyl is disubstituted in the 2, 3 or 2, 4 or 2,5 positions. Preferably both substituents are halogen more particularly, fluorine and chlorine. For example, a particularly preferred combination is 2-fluoro and 4-chloro.

In an alternative aspect the phenyl is monosubstituted by $C_{1-6}$ alkyl, for example methyl.

In a preferred aspect of the invention, $R^1$ represents phenyl optionally substituted by halogen or $C_{1-6}$alkyl, -$(alk)_n$-$C_{3-6}$ cycloalkyl optionally substituted by OH, or a $C_{5-6}$ aliphatic heterocyclic group containing one heteroatom selected from O, N or S and optionally subsituted by —$C_{1-6}$alkyl or —$CO_2C_{1-4}$alkyl.

It is to be understood that the present invention covers all combinations of particular and preferred groups mentioned above.

The process of the present invention involves the addition of acid to the reaction mixture at the start of the reaction. The addition of acid to the reaction mixture at the start of the reaction catalyses the reaction. Suitable acids include aliphatic and aromatic carboxylic acids, aliphatic and aromatic sulfonic acids, halogen acids (e.g. HCl, HBr, HI) or mineral acids (e.g. phosphoric acid, sulphuric acid, nitric acid). The acid is preferably acetic acid, p-toluenesulfonic acid, hydrochloric acid or trifluoroacetic acid, more preferably acetic acid or hydrochloric acid, most preferably acetic acid. Carboxylic acids may be used as a solvent for the amination of 6-halopurine nucleosides or added into the reaction mixture as a separate ingredient (i.e. as a catalyst). When the acid is added as a separate ingredient, suitable solvents include alcohols (MeOH, EtOH, propanol, isopropanol, t-butyl alcohol), toluene, N,N-dimethylformamide (DMF), dimethyl sulfoxide (DMSO), ethers and MeCN. The acid is preferably present in the range 5-20 mol % of the reaction mixture.

The process of the invention is suitably carried out at elevated temperature. Preferably the temperature is in the range 50-120° C., more preferably 80-120° C., most preferably 85-95° C.

Compounds of formula (II) may be prepared by any method known in the art. For example, a suitable method for the preparation of compounds of formula (II) is disclosed in WO99/67262. Compounds of formula (III) are well known in the art.

The process of the invention can be used in the preparation of compounds which are active at adenosine receptor(s), by any method known in the art, for example as described in WO99/67262 EP0322242, WO97/43300, WO99/24449, WO99/24450, WO99/24452, WO99/67262, WO98/16539 (Novo Nordisk A/S); WO98/04126 (Rhone-Poulenc Rorer Pharmaceuticals Inc.); WO98/01459 (Novo Nordisk A/S) and as shown in the Examples. The compound may be an agonist or antagonist, but is preferably an agonist. It will be understood that the process of the invention can be used either in the preparation of an intermediate or in the preparation of a final compound. A further aspect of the invention is therefore the use of the process of the invention in the preparation of a compound which is active at one or more adenosine receptors, e.g. Adenosine A1 receptor, Adenosine A2a receptor. Another aspect of the invention is the use of the process of the invention in the preparation of an Adenosine A1 agonist, e.g. (2S, 3S, 4R, 5R)-2-(5 tert-butyl-[1,3,4] oxadiazol-2-yl)-5-[6-(4-chloro-2-fluoro-phenylamino)-purin-9-yl]-tetrahydro-furan-3,4-diol.

The following examples illustrate aspects of this invention but should not be construed as limiting the scope of the invention in any way.

EXAMPLES

Example 1

(2S, 3S, 4R, 5R)-2-(5-tert-butyl-[1,3,4]oxadiazol-2-yl)-5-[6-(4-chloro-2-fluoro-phenylamino)-purin-9-yl]-tetrahydro-furan-3,4-diol

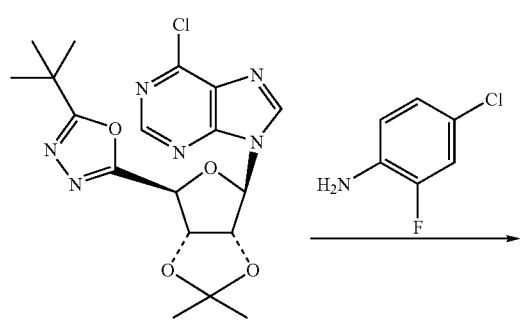

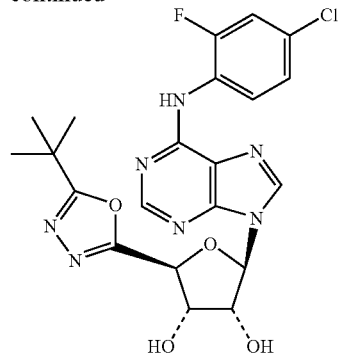

(a)

To a mixture of 40.0 g (95.1 mmol) of 9-[(3aR,4R,6S,6aS)-6-(5-tert-butyl-1,3,4-oxadiazol-2-yl)-2,2-dimethyltetrahydrofuro[3,4-d][1,3]dioxol-4-yl]-6-chloro-9H-purine and 9.52 g (95.1 mmol) of $CaCO_3$ powder was successively added 200 mL of glacial acetic acid and 21.1 mL (190 mmol) of 4-chloro-2-fluoroaniline at ambient temperature under nitrogen. The light brown mixture was heated at 76° C. for 1.5 to 2.0 h. The mixture was cooled to below 30° C. and diluted with 200 mL of toluene. The mixture was concentrated to about 120 mL by distillation at 35-45° C. under vacuum below 50 torr. This azeotropic process was repeated with a second charge of 240 mL of toluene and distilled to about 200 mL. The above mixture was filtered by suction and the filtrate was concentrated to about 80 mL at 35-45° C. under vacuum to provide a toluene solution of crude product of N-{9-[(3aR,6S,6aS)-6-(5-tert-butyl-1,3,4-oxadiazol-2-yl)-2,2-dimethyltetrahydrofuro [3,4-d][1,3]dioxol-4-yl]-9H-purin-6-yl}N-(4-chloro-2-fluorophenyl)amine.

(b)

To the above mixture was added 160 mL of 19:1 mixture of trifluoroacetic acid and water over 10 min with ice water cooling. Upon completion of the deacetonization after 22 h at 0-5° C., the reaction was quenched by addition of 800 mL of 2.5 N NaOH over 15 min with ice-water cooling. The resultant white solid was filtered. The filtering cake was washed with 500 mL of water and briefly dried to give 62.3 g of crude product containing 4-chloro-2-fluoroaniline. Recrystallization from acetonitrile provided 34.3 g (74%) of (2S, 3S, 4R, 5R)-2-(5 tert-butyl-[1,3,4]oxadiazol-2-yl)-5-[6-(4-chloro-2-fluoro-phenylamino)-purin-9-yl]-tetrahydro-furan-3,4-diol as a crystalline white solid. $^1$H NMR (300 MHz) δ 1.31 (s, 9H), 4.81 (m, 1H), 4.99 (m, 1H), 5.17 (d, J=3 Hz, 1H), 5.92 (m, 1H), 6.16 (d, J=3 Hz, 1H), 7.32 (m, 1H), 7.51 (m, 1H), 7.64 (m, 1H), 8.24 (m, 1H), 8.52 (m, 1H), 9.74 (s, 1H).

Example 2

Comparative Data

The table below shows the results of a controlled study comparing the literature method described in Fleysher, M. H. et al., *J. Med. Chem.* (1969) 12:1056 with the method of the present invention*.

*To a mixture of 300 mg (0.713 mmol) of 9-[(3aR,4R,6S,6aS)-6-(5-tert-butyl-1,3,4-oxadiazol-2-yl)-2,2-dimethyltetrahydrofuro[3,4]-[ ][1,3]dioxol-4-yl]-6-chloro-9H-purine and 0.24 mL (2.14 mmol) of 4-chloro-2-fluoroaniline in 4.7 mL of absolute ethanol was successively added 0-143 mg (0-1.43 mmol) of CaCO$_3$ powder and 0-35 μL (0-143 mmol) of 4 N HCl in 1,4-dioxane at ambient temperature. The mixture was heated at reflux and aliquot samples were taken at various time of the reaction. The samples were analysed by the HPLC method as follows. Column: Luna C18 50×2 mm, 3 μm; wavelength: 270 nm; flow rate: 1 mL/min at 40° C.; mobile phase A: H$_2$O (0.05% TFA); mobile phase B: MeCN (0.05% TFA); gradient 0-95% B over 8 min. Peaks of the starting chloropurine nucleoside, the product N-{9-[(3aR,6S,6aS)-6-(5-tert-butyl-1,3,4-oxadiazol-2-yl)-2,2-dimethyltetrahydrofuro[3,4-d[1,3]dioxol-4-yl]-9H-purin-6-yl}-N-(4-chloro-2-fluorophenyl) and three major impurities derived from decomposition of the isoxazole and acetonide moieties were examined.

Results

| Reaction conditions | Product* (AUC %) | | Starting* Material (AUC %) | | Major Impurities* (AUC %) | |
|---|---|---|---|---|---|---|
| | 1.5 h | 3.0 h | 1.5 h | 3.0 h | 1.5 h | 3.0 h |
| A Control | 5.0 | 64 | 69 | 16 | 0 | 3.2 |
| B 4N HCl (0.2 eq) | 71 | 57 | 4.6 | 0 | 10 | 27 |
| C CaCO$_3$ (2eq), 4N HCl (0.1 eq) | 69 | 73 | 8.7 | 3.2 | 4.5 | 7.7 |
| D CaCO$_3$ (2eq) | 17 | 72** | 56 | 1.2** | 0 | 11** |

*The area under curve (AUC) readings for HPLC was not adjusted for 4-chloro-2-fluoroaniline.
**These results were based on HPLC analysis after reflux for 5 hours. Data for 3.0 h is not available.

Compared with the CaCO$_3$ method described in the literature, the method of the present invention is faster. After 1.5 h, the control reaction (no CaCO$_3$, no HCl) had only 5% product, HCl reaction 71%, CaCO$_3$/HCl reaction 69% and CaCO$_3$ reaction 17%. These numbers demonstrate that addition of HCl to the reaction mixture increased reaction rate. CaCO$_3$ appeared to reduce the level of impurities (compare impurity level for reactions B and C, 10% vs. 4.5% at the 1.5$^{th}$ h and 27% vs. 7.7% at the 3$^{rd}$ h). For results at the 3 h, the last reaction (D) is not a direct comparison due to the fact the numbers in ** were taken at the 5$^{th}$ hour.

In addition to the above data, it should be noted that when acetic acid was used as catalyst/solvent in the presence of only one equivalent of CaCO$_3$, HPLC showed 87% product, 1.7% starting material and only 2.5% impurities after only 1.0 h at 76° C.

The controlled study not only confirmed the acceleration of the reaction, but also the reduction in the amount of by-product derived from the acid induced degradation.

The invention claimed is:

1. A process wherein a N$^6$-substituted aminopurine ribofuranose nucleoside of formula (I):

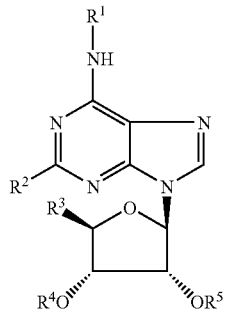

is prepared by reacting a 6-halopurine ribofuranose nucleoside of formula (II)

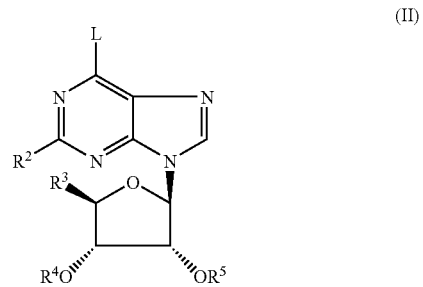

with an amine of formula (III)

H$_2$N—R$^1$    (III)

in the presence of CaCO$_3$; with acid added to the reaction mixture at the start of the reaction;
wherein in formulae (I), (II), and (III):
L is halogen;
R$^1$ is hydrogen or a group selected from:
(i) -(alk)$_n$-(C$_{3-9}$)cycloalkyl or -(alk)$_n$-(C$_{3-9}$)cycloalkenyl, said cycloalkyl or cycloalkenyl group being optionally substituted by one or more substituents selected from OH, halogen, C$_{1-6}$alkyl, —C$_{1-6}$alkoxy, C$_{2-6}$ alkenyloxy-, C$_{2-6}$alkynyloxy-, and phenyl, wherein (alk) is C$_{1-3}$alkyl and n represents 0 or 1, and said (alk) group may be optionally substituted by a C$_{3-6}$cycloalkyl group;
(ii) a phenyl group optionally substituted by one or more substituents selected from: halogen, OH, CF$_3$, cyano, —C$_{1-6}$alkyl, —C$_{2-6}$alkenyl, —C$_{2-6}$alkynyl, C$_{1-6}$alkoxy-, —C$_{1-6}$alkylOH, —CO$_2$H, and —CO$_2$C$_{1-6}$alkyl;
(iii) a C$_{4-7}$aliphatic heterocyclic group containing at least one heteroatom selected from O, N and S, and optionally substituted by one or more substituents selected from: OH, —C$_{1-6}$alkyl, —C$_{1-6}$alkoxy, —CO$_2$(C$_{1-4}$)alkyl, —CO(C$_{1-4}$)alkyl, —CO$_2$aryl, and —CO$_2$(alk)$_n$(C$_{3-6}$)cycloalkyl, wherein (alk) is C$_{1-3}$alkyl and n represents 0 or 1;
(iv) a straight or branched C$_{1-12}$alkyl group optionally substituted by one or more groups selected from phenyl, halogen, hydroxy, and C$_{3-7}$cycloalkyl, wherein one or more carbon atoms of the C$_{1-12}$alkyl group may be optionally replaced by a group independently selected from S(=O)$_n$ (where n is 0, 1 or 2) and N; and
(v) a fused bicyclic ring

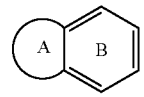

wherein A represents C$_{4-6}$cycloalkyl or phenyl and B represents phenyl optionally substituted by C$_{1-3}$alkyl, and the bicyclic ring is attached to the purine-6-amino moiety via a ring atom of ring A;
R$^2$ is C$_{1-3}$alkyl, C$_{1-3}$alkenyl, C$_{1-3}$alkoxy, halogen or hydrogen;
R$^3$ is (i) hydrogen, (ii) C$_{1-6}$alkyl optionally substituted by one or more halogens, (iii) C$_{1-6}$ alkylOCH$_2$— where the alkyl chain is optionally substituted by one or more halogens, (iv) an acetylene group, or (v) a 5-membered heterocyclic group optionally substituted by: $C_{1-6}$alkoxy-, —$C_{1-6}$alkylO(CH$_2$)$_n$— where n is 0-6, $C_{3-7}$cycloalkyl, $C_{1-6}$hydroxyalkyl, halogen, a —$C_{1-6}$alkyl, —$C_{16}$alkenyl, or —Cl$_{1-6}$alkynyl group optionally substituted by one or more halogens;

$R^4$ and $R^5$ independently are hydrogen, acyl, —$C_{1-6}$alkyl or a suitable protecting group.

2. The process according to claim 1 wherein the 6-halopurine ribofuranose nucleoside is a 6-chloropurine ribofuranose nucleoside.

3. The process according to a claim 2 wherein the acid is selected from the group consisting of aliphatic and aromatic carboxylic acids, aliphatic and aromatic sulfonic acids, halogen acids, and mineral acids.

4. The process according to claim 3 wherein the acid is acetic acid.

5. The process according to claim 4 wherein the compound of formula (I) is (2S, 3S, 4R, 5R)-2-(5-tert-butyl-[1,3,4]oxadiazol-2-yl)-5-[6-(4-chloro-2-fluoro-phenylamino)-purin-9-yl]-tetrahydro-furan-3,4-diol.

* * * * *

UNITED STATES PATENT AND TRADEMARK OFFICE
CERTIFICATE OF CORRECTION

PATENT NO. : 7,297,787 B2
APPLICATION NO. : 10/471682
DATED : November 20, 2007
INVENTOR(S) : Malcolm Berry, John C. Roberts and Shiping Xie It is certified that error appears in the above-identified patent and that said Letters Patent is hereby corrected as shown below:

On the title page and Col. 1, Line 1-3
Item (54)   TITLE should read:
   --PROCESS FOR PREPARING N6-SUBSTITUTED AMINOPURINE RIBOFURANOSE NECLEOSIDES--

Claim 1 - Column 11, Line 6 - should read:
   -- -C1-6 alkynyl group optionally substituted by one or more halogens;--

Signed and Sealed this

Twentieth Day of April, 2010

David J. Kappos
*Director of the United States Patent and Trademark Office*